United States Patent [19]
Kharitonov et al.

[11] Patent Number: 6,053,874
[45] Date of Patent: Apr. 25, 2000

[54] BREATH COLLECTION AND STORAGE

[75] Inventors: Sergei A. Kharitonov; Peter J. Barnes; Paolo Paredi, all of London; Richard Edward Kynnesley Russell, East Grinstead, all of United Kingdom

[73] Assignee: Boditech Diagnostics Limited, London, United Kingdom

[21] Appl. No.: 09/237,217

[22] Filed: Jan. 25, 1999

[51] Int. Cl.[7] .................................. A61B 5/08; A62B 7/10
[52] U.S. Cl. ...................... 600/543; 600/529; 128/205.27
[58] Field of Search ..................................... 600/543, 529; 128/201.25, 205.27, 205.29

[56] References Cited

U.S. PATENT DOCUMENTS

| | | | |
|---|---|---|---|
| 4,727,871 | 3/1988 | Smargiassi et al. | 128/205.12 |
| 5,826,575 | 10/1998 | Lall | 128/204.17 |
| 5,901,705 | 5/1999 | Leagre | 514/21 |

Primary Examiner—Cary O'Connor
Assistant Examiner—Navin Natnithitadha
Attorney, Agent, or Firm—Frommer Lawrence & Haug LLP; William S. Frommer

[57] ABSTRACT

A breath sample reservoir comprises a container for storing a sample of breath, the container defining a sealable aperture through which the breath sample can be introduced into the container, the container being provided with a bactericidal material to inhibit reproduction of bacteria within the container.

10 Claims, 1 Drawing Sheet

BREATH COLLECTION AND STORAGE

BACKGROUND OF THE INVENTION

1. Field of the Invention

This invention relates to apparatus and methods for breath collection and storage.

2. Description of the Prior Art

Recently there has been increasing interest in diagnostic and other measurements of the level of various components in exhaled breath. For example, it has been recognised that a measurement of the level of nitric oxide (NO) in exhaled breath can give a diagnostic indicator of the patient's lung condition, such as a degree of lung inflammation in asthma sufferers.

A difficulty in many of these measurements is that the breath sample may contain a very low level of the breath component of interest. For example, a healthy patient may have a breath NO level of about 7 ppb (parts per billion), while in an asthma sufferer the level may still be as low as under 100 ppb. These low levels and the need for clinical accuracy can mean that the measurement equipment is bulky, expensive and relatively fragile.

As a result, a two-stage technique has been developed, involving a remote collection of a breath sample, for example at a family doctor's premises or even in the patient's home, followed by later analysis of the sample at a central site such as a hospital, where the detection apparatus can be kept and maintained.

A polyethylene-lined collection and storage bag or reservoir has been proposed, whereby the patient exhales through a mouthpiece and detachable tube into an inflatable bag. The bag is then sealed. The breath sample can then be analysed later by puncturing the bag to transfer the stored sample into an analysis machine.

SUMMARY OF THE INVENTION

This invention provides a breath sample reservoir comprising a container for storing a sample of breath, the container defining a sealable aperture through which the breath sample can be introduced into the container, the container being provided with a bactericidal material to inhibit reproduction of bacteria within the container.

The invention recognises a problem with the use of previously proposed breath sample bags or reservoirs, in that during the time that the breath sample is within the bag the sample may deteriorate through the action of living organisms such as bacteria present in the breath. These can continue to survive and to grow inside the bag, and car often give off NO or other gases of interest as part of their life cycle. This bacteria-induced gas can interfere with the detection of the gas originally present in the breath sample.

The invention addresses this problem by providing a bactericidal material to inhibit reproduction of bacteria within the container.

BRIEF DESCRIPTION OF THE DRAWINGS

The above and other objects, features and advantages of the invention will be apparent from the following detailed description of illustrative embodiments which is to bit read in connection with the accompanying drawings, in which.

DESCRIPTION OF THE PREFERRED EMBODIMENTS

Figure 1:
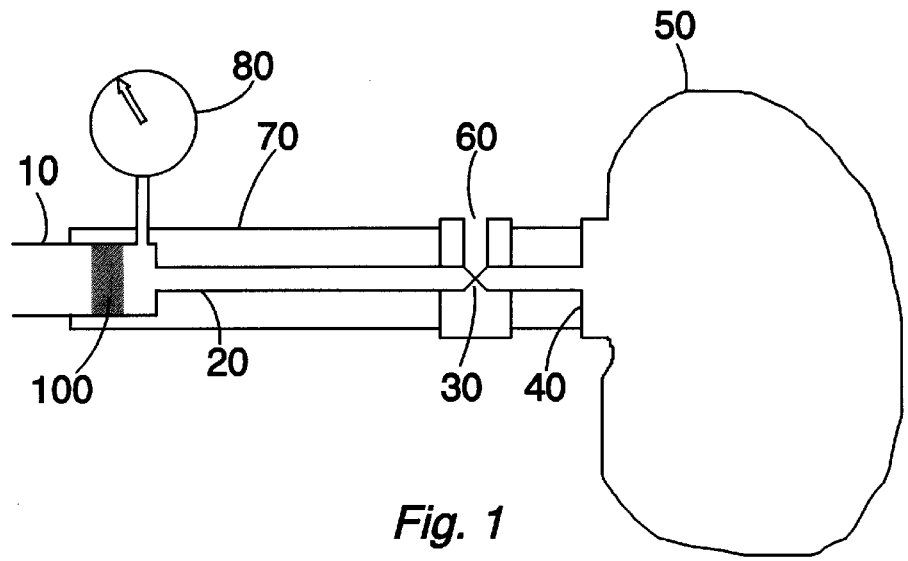
FIG. 1 is a schematic diagram of a first embodiment of a breath sample reservoir.

Referring now to FIG. 1, a breath sample reservoir comprises a mouthpiece 10 connected by a constricted tube 20 and a valve 30 to the inlet 40 of a flexible sack 50 forming a container for the breath sample. The valve 30 is operable to route air flowing along the tube 20 either to the container 50 or to an atmospheric vent 60. A hand grip 70 is provided around the tube 20, and a pressure meter 80 gives an indication of the pressure at which the patient's breath is being applied to the apparatus.

An anti-bacterial filter 100 is disposed within the mouthpiece. This will be described in more detail below.

In operation, the patient (not shown) places the mouthpiece 10 into his (her) mouth. The container 50 is initially in a deflated condition. The patient blows into the mouthpiece 10 and attempts to keep the pressure gauge 80 at a predetermined pressure reading (e.g. 10 cm $H_2O$ at an exhalation flow of 10–11 liters/minute).

For an initial period of the exhalation, the valve 30 is set by the user or another operator to vent the air to the atmospheric vent 60 rather than into the container 50. This measure is established practice within the medical field when breath samples are being studied for NO levels or other gasses, in order to discard air from the so-called "dead space", that is, the area of the upper airways over which gas exchange does not take place. After this "dead space" air has been discarded, the valve 30 is adjusted to route subsequent exhalation into the container 50 rather than to the atmospheric vent 60. In this way, the air directed into the container 50 comes primarily from the alveoli rather than from the "dead space", giving a more representative reading of the NO level in the lungs.

The tube 20 is of narrower diameter than the mouthpiece. In this embodiment, some example dimensions are an interior diameter of 27 mm for the mouthpiece and an interior diameter of 5mm for the tube 20. This change in diameter generates a flow restriction and, in use applies a back pressure against the breath being exhaled into the reservoir apparatus. Again, this is a conventional step in the field of NO detection, in that the application of the back pressure tends to close the patient's soft palate and avoid contamination by nasal air.

When a sufficiently large sample has been collected, the container 50 is detached at the inlet 40 and sealed. It can then be taken to a remote site (e.g. a hospital) where the container may be punctured and the air inside tested for levels of gasses such as NO.

The time period between the sample being taken and its later analysis will depend on the nature of the clinical work being undertaken and the geographical separation of the patient from the hospital. It is not unusual for this time delay to be of the order of 24 hours. During that time, we have observed that bacteria present in a normal adult's breath can distort a subsequent measure of the NO level in a breath sample, by actually generating further NO as part of their metabolic processes during the storage period.

In one experiment we have undertaken, a breath sample for which the measurement of NO level was carried out immediately was found to have a level of 7.9 ppb, whereas after 24 hours' storage in a container (without the filter 100) at room temperature, the detected NO level of the stored sample was found to be 21.6 ppb. So, there was almost a 200% increase in NO provided by the reaction of breath-carried bacteria during the 24 hour storage period. This means that the true results for that patient would be completely masked by the artifacts caused by the storage of the breath sample.

These errors are very difficult to calibrate out, as the amount of bacteria-generated NO in a stored sample will depend on many factors including the bacteria content of the initial breath sample, the storage temperature, the storage time and other storage conditions. Accordingly, we have devised various measures to alleviate or overcome this problem.

An example of this is illustrated in FIG. 1, namely the anti-bacteria filter 100. Providing an anti-bacterial agent of this nature at the input to the reservoir apparatus can dramatically reduce the bacteria content of the air to be stored in the container 50. The anti-bacteria filter 100 is preferably disposable (e.g. along with a disposable mouthpiece 10) so that the effect of this measure is not diminished by repeated uses of the apparatus.

In a similar experiment to the one described above, we obtained an NO level of 7.6 ppb at the time of sampling, and, using a filtered storage reservoir of the type shown in FIG. 1, we obtained an NO level of 10.4 ppb after a storage period of 24 hours at room temperature. So, the bacteria-induced NO generation has been dramatically reduced in comparison to the unfiltered case described above.

Figure 2:
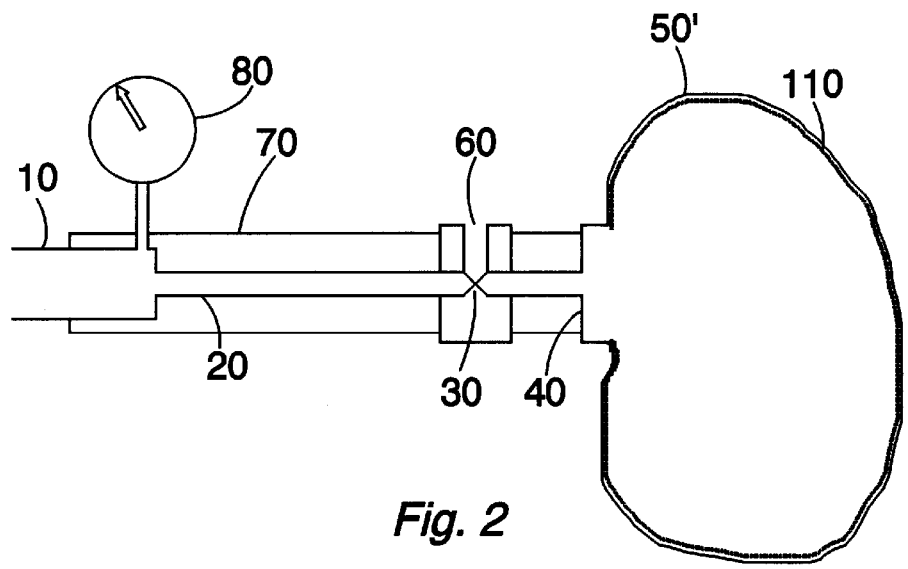
FIG. 2 is a schematic diagram of a second embodiment of a breath sample reservoir.

FIG. 2 illustrates another measure which can reduce the effect of breath-carried bacteria on delayed NO measurement, which is the provision of a bactericidal lining or coating 110 on the interior of the container 50'. The lining or coating could be an antibiotic such as tetracyclin or an antiseptic such as Milton (TM) fluid or alcohol. In alternative embodiments, the anti-bacterial agent within the container 50' could be loose in powder or liquid form, although in this case care has to be taken so that the agent does not damage the analyser used to analyse the breath content of the container 50'.

Figure 3:
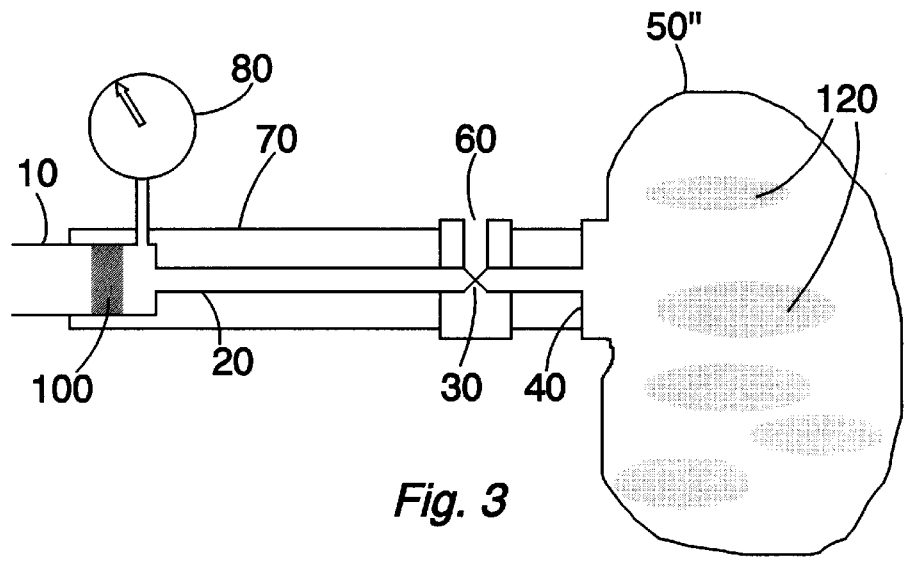
FIG. 3 is a schematic diagram of a third embodiment of a breath sample reservoir.

Finally, FIG. 3 illustrates a third embodiment of a breath sample reservoir employing an anti-bacterial filter 100 as shown in FIG. 1, in conjunction with a desiccant material 120 forming either a coating inside the container 50" or placed loose within that container. The desiccant material 120 could be, for example, silica gel desiccant. This can serve to dry the stored air, and, in addition to the lack of moisture inhibiting bacterial activity the general quality of the stored air can be improved by desiccation.

The desiccant material 120 of FIG. 3 could instead (or in addition) be used with the filter 100 of FIG. 1. Similarly, the embodiments of FIGS. 1 and 2 could be combined to provide a system having a filter as well as an anti-bacterial agent inside the container.

The filter of FIG. 1 could be disposed at any position within the air flow path defined between the entry to the mouthpiece and the entry to the container 50. However, for a hygiene improvement it is preferred that the filter is part of the mouthpiece, so that this whole unit may be made disposable (i.e. for one use only). In any event the filter is preferably disposed towards the input of the apparatus so that bacterial ingress to the remainder of the apparatus can be reduced.

The storage properties of the breath samples stored in these embodiments of the invention can be improved further by cooling the container during the storage period.

Apart from combinations explicitly defined by the appended claims, other permutations of features of the invention and its embodiments may be made.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

We claim:

1. A breath sample reservoir comprising a container for storing a sample of breath, the container defining a sealable aperture through which the breath sample can be introduced into the container, the container being provided with a bactericidal material to inhibit reproduction of bacteria within the container.

2. A reservoir according to claim 1, in which the container is a flexible sack.

3. A reservoir according to claim 1, the container having an interior surface, at least part of the interior surface of the container being coated in the bactericidal material.

4. A reservoir according to claim 3, in which the bactericidal material comprises at least an antibiotic compound.

5. A reservoir according to claim 3, in which the bactericidal material comprises at least an antiseptic agent.

6. A reservoir according to claim 1, in which the container is provided with an inlet conduit to define an air flow path from a patient's mouth to the container.

7. A reservoir according to claim 6, in which the bactericidal material is in the form of a bacteria filter disposed in said air flow path, to inhibit entry of bacteria into said container.

8. A reservoir according to claim 7, in which said bacteria filter is disposed at a position towards a breath input of said air flow path.

9. A reservoir according to claim 7, in which said bacteria filter is disposed within said mouthpiece.

10. A reservoir according to claim 1, comprising a desiccant material disposed inside said container.

\* \* \* \* \*